US 6,629,879 B1

(12) United States Patent
Kim et al.

(10) Patent No.: US 6,629,879 B1
(45) Date of Patent: Oct. 7, 2003

(54) METHOD OF CONTROLLING BARRIER METAL POLISHING PROCESSES BASED UPON X-RAY FLUORESCENCE MEASUREMENTS

(75) Inventors: Susan Kim, Austin, TX (US); Paul R. Besser, Sunnyvale, CA (US)

(73) Assignee: Advanced Micro Devices, Inc., Austin, TX (US)

( * ) Notice: Subject to any disclaimer, the term of this patent is extended or adjusted under 35 U.S.C. 154(b) by 52 days.

(21) Appl. No.: 09/851,459

(22) Filed: May 8, 2001

(51) Int. Cl.⁷ .................................................. B24B 1/00
(52) U.S. Cl. ........................... 451/57; 451/41; 451/6; 451/53; 438/692; 438/693
(58) Field of Search ................. 451/57, 41, 6, 451/53, 8; 438/692, 693; 378/50, 45, 76, 88, 89, 70

(56) References Cited

U.S. PATENT DOCUMENTS

| | | | | |
|---|---|---|---|---|
| 5,461,654 A | * | 10/1995 | Grodzins et al. | 378/45 |
| 5,483,568 A | * | 1/1996 | Yano et al. | 378/44 |
| 6,062,949 A | * | 5/2000 | Yashiki et al. | 451/10 |
| 6,130,931 A | * | 10/2000 | Laurila et al. | 378/45 |
| 6,173,036 B1 | * | 1/2001 | Hossain et al. | 378/45 |
| 6,213,847 B1 | * | 4/2001 | Torii | 451/18 |
| 6,234,875 B1 | * | 5/2001 | Pendergrass, Jr. | 451/41 |
| 6,256,373 B1 | * | 7/2001 | Bernstein et al. | 378/45 |
| 6,258,231 B1 | * | 7/2001 | Easter et al. | 204/421 |
| 6,261,157 B1 | * | 7/2001 | Bajaj et al. | 451/57 |
| 6,266,390 B1 | * | 7/2001 | Sommer et al. | 378/45 |
| 6,290,572 B1 | * | 9/2001 | Hofmann | 451/5 |
| 6,376,267 B1 | * | 4/2002 | Noack et al. | 438/16 |

OTHER PUBLICATIONS

"What is EDXRF?," KevexSpectrace, http://www.kevex-spectrace.com/edxrf.htm, 2001.
"X–ray Fluorescence Fundamentals," KevexSpectrace, http://www.kevexspectrace.com/edxrf_theory.htm, 2001.
"Components of the XRF Spectrometer," KevexSpectrace, http://www.kevexspectrace.com/edxrf_hardware.htm, 2001.

* cited by examiner

Primary Examiner—Lee D. Wilson
(74) Attorney, Agent, or Firm—Williams, Morgan & Amerson

(57) ABSTRACT

The present invention is directed to a method of controlling polishing processes based upon x-ray fluorescence measurements. In one illustrative embodiment, the method comprises providing a wafer comprised of a layer of insulating material having a barrier metal layer formed thereabove and a layer of copper formed above the barrier metal layer, performing a chemical mechanical polishing operation to remove the barrier metal layer, irradiating at least one area of the wafer with x-rays, and analyzing x-rays leaving the irradiated area to determine the presence of material comprising the barrier metal layer.

27 Claims, 3 Drawing Sheets

METHOD OF CONTROLLING BARRIER METAL POLISHING PROCESSES BASED UPON X-RAY FLUORESCENCE MEASUREMENTS

BACKGROUND OF THE INVENTION

1. Field of the Invention

The present invention is generally directed to the field of semiconductor manufacturing, and, more particularly, to a method of controlling barrier metal polishing processes based upon x-ray fluorescence measurements.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

In modem integrated circuit devices, millions of transistors are formed above a surface of a semiconducting substrate. To perform their intended functions, these transistors, or groups of transistors, are electrically coupled together by many levels of conductive inter-connections, i.e., conductive metal lines and plugs. These conductive lines and plugs allow electrical signals to propagate throughout the integrated circuit device. In general, these conductive interconnections are formed in layers of insulating material, e.g., silicon dioxide, HSQ, or other materials that may have a dielectric constant less than approximately 4. The insulating materials electrically isolate the various conductive inter-connections and tend to reduce capacitive coupling between adjacent metal lines when the integrated circuit device is in operation.

As the demand for high performance integrated circuit devices continues to increase, circuit designers and manufacturers look for ways to improve device performance. Recently, copper has become the material of choice for conductive interconnections for high performance integrated circuit devices, e.g., microprocessors, due to its lower resistance as compared to, for example, aluminum.

Conductive interconnections comprised of copper may be formed using a variety of process flows, e.g., single damascene, dual damascene, etc. For example, a layer of insulating material may be formed on or above a semiconducting substrate. Thereafter, a plurality of openings may be formed in the layer of insulating material using known photolithographic and etching techniques. Then, a relatively thin barrier metal layer comprised of, for example, tantalum, is conformally deposited above the insulating layer and in the openings in the insulating layer. Next, a relatively thin layer of copper, a so-called copper seed layer, is deposited on the barrier metal layer. A much thicker layer of copper is then formed by using known electroplating techniques. This final layer of copper will fill the remaining portions of the openings in the insulating layer, and have an upper surface that extends above the surface of the insulating layer.

Ultimately, one or more chemical mechanical polishing (CMP) operations will be performed to remove the excess copper and barrier layer material from above the surface of the insulating layer. This process results in the definition of a plurality of conductive inter-connections, e.g., conductive lines or plugs, or a combination of both, positioned within the openings in the insulating layer. Such chemical mechanical polishing operations may involve a sequence of polishing operations. For example, the bulk of the excess copper may be removed during an initial, timed polishing process. The removal rate during the initial timed polishing process may be relatively high. Thereafter, an endpoint polish process may be performed to remove the remaining copper material. The removal rate during this endpoint process may be relatively low. The endpoint of this portion of the process may be detected through use of an optical sensor, such as a laser-type system whereby the intensity of light reflected off of the wafer is measured. Additional polishing operations may be performed to remove the barrier layer material.

As set forth above, chemical mechanical polishing is an important process as it relates to the formation of conductive interconnections comprised of copper in modern integrated circuit devices. A variety of chemical mechanical polishing tools are commercially available. In all such systems, the object is to polish the surface of a process layer, e.g., copper, with a polishing pad in the presence of a polishing slurry. In general, chemical mechanical polishing involves the selective removal of all or portions of the process layer or film from the wafer through chemical reactivity of the polishing slurry used during the process, and the mechanical abrasion of the process layer due to its contact with the polishing pad. For example, the chemical component of the CMP process is dependent on the chemistry, concentration and pH of the polishing slurry. Furthermore, the mechanical abrasion is dependent on, among other things, the slurry particle size and concentration, polishing pad hardness and surface roughness, pad pressure, and the rotational speeds of the wafer and the pad. All of these variables tend to make accurately controlling CMP processes difficult.

As set forth above, the polishing of copper is typically accomplished in multistage polishing systems. For example, bulk copper removal (at relatively high rates) may be performed at a first stage, additional copper removal (at relatively slower rates) may be performed at a second stage, and a third stage may be used for removal of any underlying barrier layer material. However, due to the many variables encountered in CMP processes, the removal of the copper material may be less than complete across the entire surface of the wafer. More particularly, it is difficult to detect if all of the copper material has been removed before the wafers are moved to the polishing stage where it is intended that the barrier metal material be removed. More importantly, the existence of the residual copper may inhibit removal of the barrier layer material. Over-polishing in an attempt to insure that all of the copper is removed is undesirable in that it may result in an undesirable level of dishing of the resulting metal lines and otherwise produce across-wafer non-uniformities. Under-polishing can produce undesirable surface topographies and may lead to electrical shorts if sufficient quantities of residual copper remain above the insulating layer. Similarly, it is difficult to detect when all of the barrier metal layer has been removed by polishing. Over-polishing the barrier metal layer to insure complete removal of the barrier layer is undesirable in that it may lead to excessive erosion of the underlying insulating layer, and it may tend to reduce the thickness of the conductive interconnection beyond acceptable limits.

Additionally, in traditional CMP tools, after polishing operations are believed to be complete, the wafer is subjected to a post-CMP clean process and measured to determine if all of the layer under consideration, e.g., copper layer, barrier metal layer, was removed. If not, the incompletely polished wafer must be returned to the CMP tool for further polishing operations. All of these steps lead to increased product cycle times and reduced yields.

The present invention is directed to a method that may solve, or at least reduce, some or all of the aforementioned problems.

SUMMARY OF THE INVENTION

The present invention is directed to a method of controlling barrier metal polishing processes based upon x-ray fluorescence measurements. In one illustrative embodiment, the method comprises providing a wafer comprised of a layer of insulating material having a barrier metal layer formed thereabove, performing a chemical mechanical polishing operation to remove the barrier metal layer material from above the insulating layer, irradiating at least one area of the wafer with x-rays, and analyzing x-rays leaving the irradiated area to determine the presence of the barrier metal layer material. In a further embodiment, the method comprises examining an x-ray spectrum of the x-rays leaving the irradiated area for the presence of the barrier metal layer material.

BRIEF DESCRIPTION OF THE DRAWINGS

The invention may be understood by reference to the following description taken in conjunction with the accompanying drawings, in which like reference numerals identify like elements, and in which.

Figure 1:
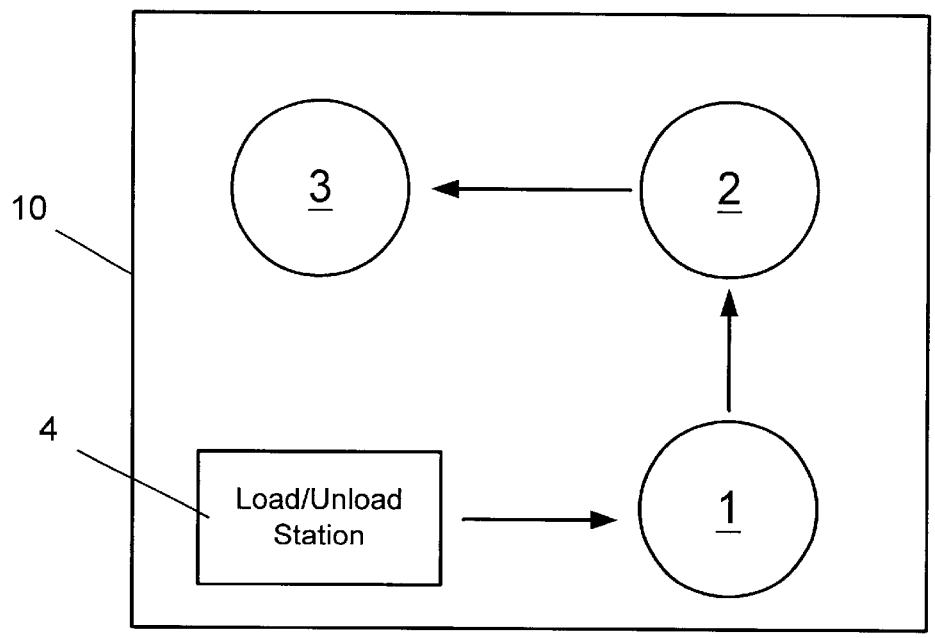
FIG. 1 is schematic view of an illustrative polishing tool that may be used with the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention.

In general, the present invention is directed to a method of controlling polishing processes based upon x-ray fluorescence measurements. As will be readily apparent to those skilled in the art upon a complete reading of the present application, the present method is applicable to a variety of technologies, e.g., NMOS, PMOS, CMOS, etc., is readily applicable to a variety of devices, including, but not limited to, logic devices, memory devices, etc.

As stated previously, forming integrated circuit devices having conductive interconnections comprised of copper typically involves multistage polishing operations. A variety of tools are commercially available for performing such polishing operations, and may be used with the present invention. FIG. 1 is a schematic description of one such illustrative tool, an Applied Materials Mirra copper polishing tool. The Applied Materials tool may be purchased from Applied Materials located in Santa Clara, Calif. In this particular embodiment, the polishing tool 10 is comprised of three polishing platens, platen 1, platen 2 and platen 3, and a load/unload station 4. In general, as described more fully below, each wafer is subjected to various polishing operations at each of the platens 1–3. Wafers are processed at all four stations, i.e., platens 1–3 and the load/unload station 4, in parallel. After completion of the longest process time, all wafers are moved to the next station. However, the polishing tool 10 need not involve multiple processes to remove the copper material. That is, the present invention may be employed in situations where it is intended that substantially all of the copper material be removed at a first stage of the polishing tool 10. Additionally, after a complete reading of the present application, those skilled in the art will understand that the present invention may be employed with systems and processes other than standard CMP systems and processes. For example, the present invention may be employed in fixed abrasive or reactive liquid-type systems.

Figure 2:
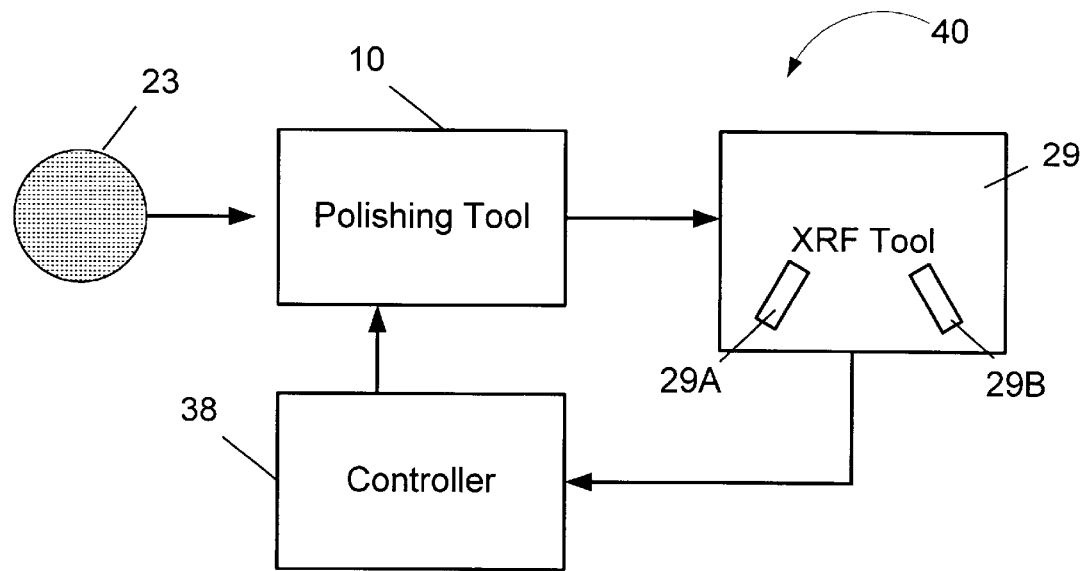
FIG. 2 is a schematic depiction of one embodiment of a system in which the present invention may be employed.

In general, the present invention is directed to the use of x-ray fluorescence (XRF) measurements to control certain aspects of the CMP processes used to remove copper material and the barrier metal layers commonly employed in manufacturing conductive inter-connections comprised of copper. FIG. 2 depicts an illustrative system 40 that may be used with the present invention. In the depicted embodiment, the system 40 is comprised of a polishing tool 10, an x-ray fluorescence tool 29 and a controller 38. The polishing tool 10 may be any type of polishing tool useful for removing copper, and/or the barrier layer material. The controller 38 may be a stand-alone controller resident somewhere in the manufacturing facility, or it may be a controller resident on the polishing tool 10 and/or the XRF tool 29. The XRF tool 29 may be a separate stand-alone tool, it may be mounted in situ with the polishing tool 10, or it may be as a separate chamber or station within the polishing tool 10.

The XRF tool 29 may be any type of tool useful for producing x-ray fluorescence metrology data that will enable detection of the presence of copper and/or of the barrier layer material on the wafer 23. As schematically depicted in FIG. 2, the XRF tool 29 is comprised of an x-ray source 29A (typically an x-ray tube) and a detector 29B. The XRF tool 29 will be used to irradiate one or more areas of a wafer. X-ray fluorescence measurements involve using ionizing radiation to excite the sample within the irradiated area, and detecting and measuring the x-rays leaving the sampled area that are characteristic of the elements in the sample. The collector 29B is used to collect the x-rays leaving the sample. In one illustrative embodiment, the XRF tool 29 may be an Omicron manufactured by Kevex of Redwood, Calif.

Using x-ray fluorescence technology, different materials fluoresce at different wavelengths. For example, copper fluoresces at an energy of approximately 8.047 keV. Thus, through use of the XRF tool 29, the system 40 may be used to detect the presence or absence of copper during or after the polishing operations that are performed to remove the copper material. The XRF tool 29 may also be used to detect the presence of various materials that may be employed at a barrier metal. For example, the XRF tool 29 may be used to detect the presence of tantalum, a barrier metal layer commonly used in making conductive interconnections comprised of copper at the point in the polishing process where the barrier metal layer is to be removed. Tantalum fluoresces at an energy of approximately 8.145 keV. The secondary beta peaks for copper and tantalum occur at 8.904 and 9.341 keV, respectively.

Figure 3:
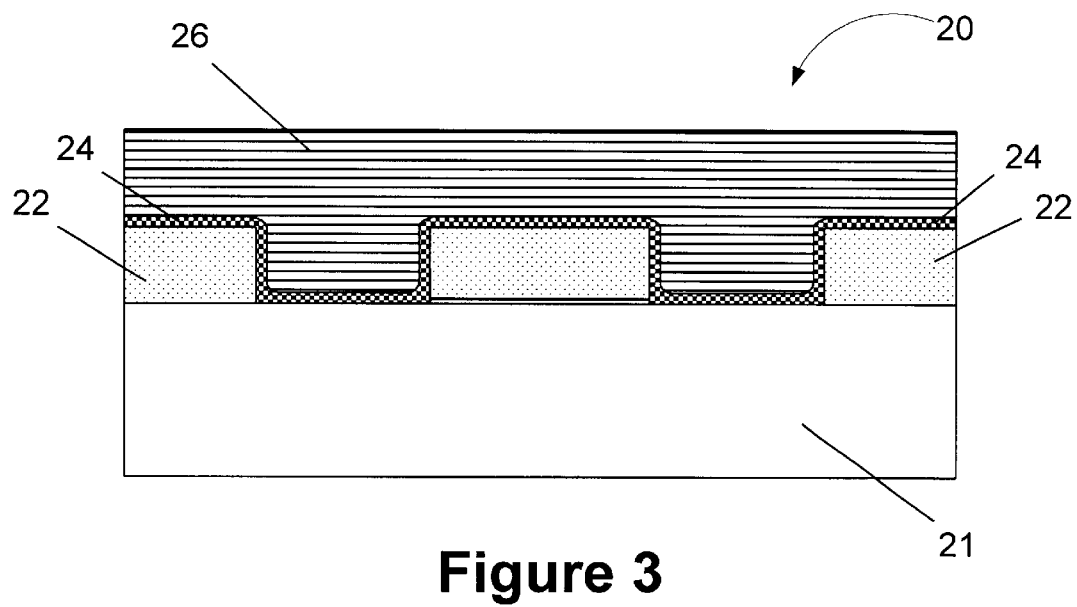
FIG. 3 is a cross-sectional view of a partially formed integrated circuit device comprised of a layer of metal formed above a patterned layer of insulating material.

FIGS. 3–6 are cross-sectional views of a partially formed integrated circuit device 20 that will be used to describe the various polishing operations performed at each of the platens 1–3, and to describe how the present invention disclosed herein may be employed in controlling such operations. As shown in FIG. 3, the partially formed integrated circuit device 20 is comprised of a patterned layer of insulating material 22 formed above a structure 21, a barrier metal layer 24, and a layer of metal 26, e.g., copper. The structure 21 is intended to be representative in nature in that it may be a semiconducting substrate, a previously formed layer of material, e.g., a layer of silicon dioxide, or a previously formed stack of layers of insulating material having a plurality of conductive interconnections formed in each layer.

The various layers depicted in FIG. 3 may be comprised of a variety of materials, and they may be formed by a variety of techniques. For example, the structure 21 may be a previously formed layer of silicon dioxide that is formed by a chemical vapor deposition ("CVD") process using TEOS as a constituent gas, and it may have a thickness ranging, for example, from approximately 100–800 nm. The patterned layer of insulating material 22 may be formed from a variety of materials, e.g., silicon dioxide, silicon nitride, HSQ, materials having a dielectric constant less than 4, etc. The patterned layer of insulating material 22 may be formed by blanket depositing a layer of insulating material, and, thereafter, patterning the layer of material using known photolithography and etching techniques to result in the patterned layer of insulating material 22 shown in FIG. 3.

Thereafter, the barrier metal layer 24 may be conformally deposited above the patterned layer of insulating material 22 using a variety of process methods, e.g., CVD, plasma enhanced CVD ("PECVD"), physical vapor deposition ("PVD"), sputtering, etc. The barrier metal layer 24 may be comprised of a variety of materials, e.g., tantalum, tantalum nitride, titanium nitride, tungsten nitride, titanium nitride silicon, tantalum silicon nitride, etc., and its thickness may vary. In one illustrative embodiment, where conductive interconnections comprised of copper are being formed, the barrier metal layer 24 is comprised of tantalum, and it may have a thickness ranging, for example, from approximately 5–40 nm.

Thereafter, the metal layer 26 comprised of, for example, copper, is formed above the barrier metal layer 24 by known electroplating techniques. Typically, in the case where the metal layer 26 is comprised of copper, this process involves the formation of a copper seed layer (not shown) above the barrier metal layer 24, and, thereafter, positioning the partially formed integrated circuit device 20 in an electroplating bath to form the metal layer 26 comprised of copper. The copper layer 26 may have a thickness (above the patterned insulating layer 22) that ranges, for example, from approximately 200–1000 nm.

Figure 4:
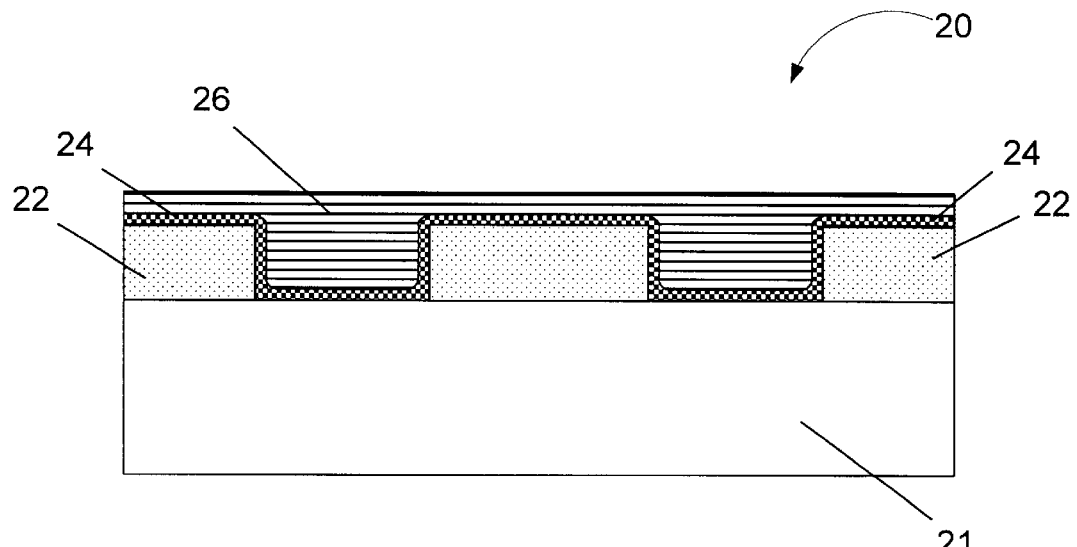
FIG. 4 is a cross-sectional view of the device shown in FIG. 3 after a majority of the layer of metal has been removed at a first polishing platen of the polishing tool.

The present invention will now be further described with reference to the specific embodiment wherein the metal layer 26 is comprised of copper. However, the present invention should not be considered as limited to the polishing of copper unless such limitation is clearly set forth in the appended claims. At platen 1 of the polishing tool 10, a majority, and typically the bulk, of the copper layer 26 is removed. A relatively high polisher arm down-force is used to achieve an aggressive removal rate on the order of approximately 8–16 nm/sec (80–160 Å/sec) of copper. In one embodiment, the polishing process performed at platen 1 is a timed process whereby, in one application, approximately 50–80% of the copper layer 26 above the patterned layer of insulating material 22 is removed. FIG. 4 depicts the wafer after polishing operations have been completed at platen 1.

Figure 5:
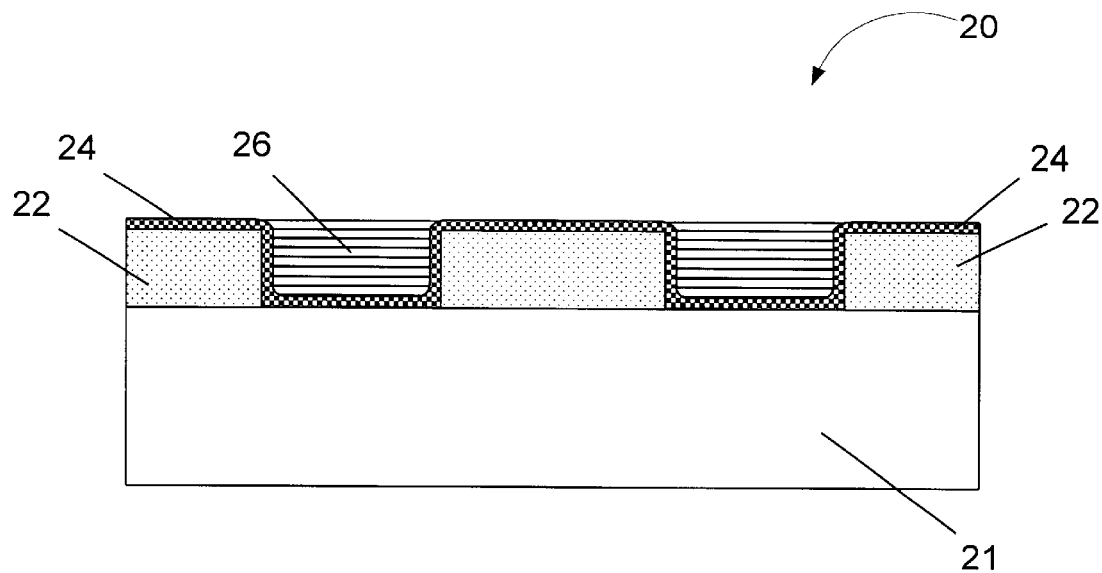
FIG. 5 is a cross-sectional view of the device shown in FIG. 4 after the remaining portions of the layer of metal have been removed at a second polishing platen of the polishing tool.
Figure 6:
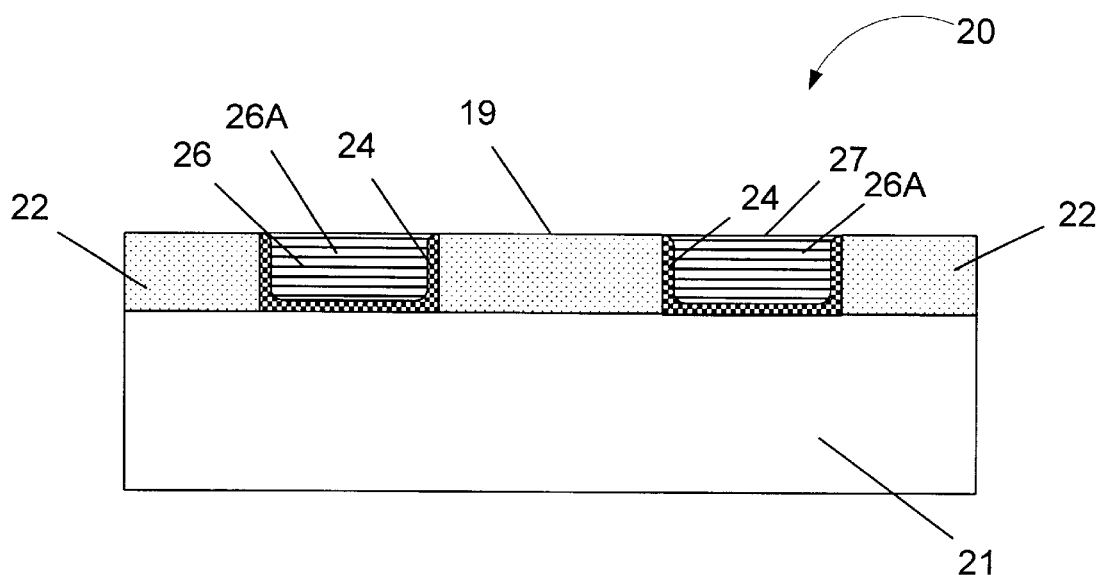
FIG. 6 is a cross-sectional view of the device shown in FIG. 5 after further polishing operations have been performed at a third polishing platen of the tool to remove the barrier layer positioned above the patterned layer of insulating material.

At platen 2, the remaining copper layer 26 is removed at a much slower rate, e.g., on the order of approximately 6–10 nm/sec (60–100 Å/sec) by the use of a lower down-force pressure. That is, polishing operations are performed at platen 2 until such time as substantially all of the copper layer 26 has been removed from above the barrier metal layer 24. Successful polishing operations at platen 2 result in the structure depicted in FIG. 5. As described more fully below, XRF metrology data may be used to endpoint the polishing operation at platen 2 and/or to confirm that polishing operations at platen 2 have been successfully completed, thereby exposing the barrier metal layer 24. Moreover, traditional optical endpointing techniques and systems may be used in addition to and in combination with the XRF metrology techniques described herein. FIG. 5 depicts the partially formed integrated circuit device 20 after polishing operations have been completed at platen 2.

At platen 3, polishing operations are performed until such time as substantially all of the barrier metal layer 24 is removed from above the surface 19 of the insulating layer 22. Note that, during this process, some of the copper positioned within the openings in the insulating layer 22 will also be removed. Successful polishing operations at platen 3 will result in the structure depicted in FIG. 6, wherein a plurality of conductive interconnections 26A, e.g., conductive copper lines, are formed in the openings in the insulating layer 22. Note that, the conductive interconnections 26A have a surface 27 that is approximately planar with the surface 19 of the insulating layer 22. It should also be noted that the attached drawings do not show any dishing of the conductive interconnections 26A, or erosion of the insulating layer 22, although such conditions may likely occur, at least to some degree, in fabricated devices. As described more fully below, XRF metrology data may be used to endpoint polishing operations at platen 3 and/or to confirm that polishing operations performed at platen 3 were successfully completed, i.e., that substantially all of the barrier metal layer 24 was successfully removed at platen 3.

As set forth previously, the XRF tool 29 may be used to endpoint operations at platens 2 and 3 and/or to confirm that the polishing operations at those platens have been successfully completed. The physical structure of a system employing the present invention may take on a variety of forms. For example, in one illustrative embodiment, the XRF tool 29 may be integrated into a separate chamber (not shown) of the polishing tool 10. In this embodiment, wafers 23 could be sent to the XRF chamber to obtain XRF metrology data at any point in the process. For example, after polishing operations have been completed at platen 2, the wafer may be subjected to XRF measurements to confirm that the polishing operations at platen 2 were successfully performed prior to allowing the wafer to be processed at platen 3. If the XRF metrology data indicates that unacceptable levels of copper still remain, the wafer 23 may be returned to platen 2 for additional polishing operations to insure substantially all of the copper is removed. In a similar fashion, after polishing operations are completed at platen 3, the wafer may be moved to the XRF chamber (not shown) to confirm that polishing operations at platen 3 were successfully performed. If the XRF metrology data indicates that removal of the barrier metal layer 24 is incomplete, the wafer may be returned to platen 3 for further polishing operations. Using this processing technique, the cycle time for producing a wafer having the desired layer removed may be decreased, i.e., the wafer may not need to be removed from the polishing tool 10 to determine the completeness of the polishing operations.

However, it should be understood that the present invention need not be employed at every step of the multistage polishing process described above. For example, the techniques described herein may only be employed to confirm the completeness of the copper removal process at platen 2. In that embodiment, the XRF chamber (not shown) may be physically positioned between platens 2 and 3. Similarly, the present invention may only be used to confirm the removal of the barrier metal layer 24 at platen 3. In that embodiment, the XRF chamber (not shown) may be physically located after platen 3.

Moreover, in other embodiments, the present invention may be used to endpoint the various polishing operations described above. That is, for example, the XRF tool 29 may be integrated into the polishing operations performed at platen 2 and the XRF metrology data may be used to endpoint the polishing operations performed at platen 2. Similarly, the XRF tool 29 may be used to endpoint the polishing operations at platen 3. Of course, the present invention may be used in conjunction with, or in addition to, optical endpointing systems employed on such polishing tools 10. That is, polishing operations at platen 2 may be endpointed through use of an optical sensor. Thereafter, the XRF tool 29 may be used to confirm the completeness of the copper removal operations performed at platen 2. Similarly, polishing operations at platen 3 may be endpointed through use of an optical sensor. Thereafter, the XRF tool 29 may be used to confirm the completeness of the barrier layer removal operations at platen 3.

The present invention may also be employed in situations where the XRF tool 29 is a stand-alone processing tool. In that embodiment, after wafers 23 are processed at platen 2, they may then be transferred to the XRF tool 29 where the appropriate XRF metrology data is obtained. For example, after polishing operations are complete at platen 2, the wafer 23 may be transported to the XRF tool 29 to determine if the operations at platen 2 were successful. If not, the wafer is returned to platen 2 for further processing. If the results are acceptable, then the wafer may be allowed to pass to platen 3 for further processing. Similarly, after polishing operations at platen 3 are complete, the wafer 23 may be transferred to the XRF tool 29 to determine if the removal of the barrier layer material was complete.

The number of sites selected per wafer to be irradiated, as well as the location of those sites, may be varied as a matter of design choice. For example, in some applications, the process engineer may determine that only a single site on a wafer need be analyzed using XRF techniques. Other applications may require more metrology data. For example, five sites on a wafer may be measured, one in the approximate center of the wafer and at four other sites spaced around the periphery of the wafer approximately 90° apart. Additionally, it may be appropriate to have more test sites in regions with densely packed metal lines as compared to regions with relatively few copper structures. The size of the irradiated areas may also vary, e.g., each of the irradiated areas may have a diameter ranging from approximately 100 $\mu$m–200 mm.

In the illustrated embodiment, the controller 38 is a computer programmed with software to implement the functions described herein. Moreover, the functions described for the controller 38 may be performed by one or more controllers spread throughout the system. For example, the controller 38 may be a fab level controller that is used to control processing operations throughout all or a portion of a semiconductor manufacturing facility. Alternatively, the controller 38 may be a lower level computer that controls only portions or cells of the manufacturing facility. Moreover, the controller 38 may be a stand-alone device, or it may reside on the polishing tool 10. However, as will be appreciated by those of ordinary skill in the art, a hardware controller (not shown) designed to implement the particular functions may also be used. The XRF tool 29 may also have a separate controller (not shown) to analyze the x-ray metrology data. Moreover, in some embodiments, e.g., where the XRF tool 29 is integrated with the polishing tool 10, the various functions described herein may be performed by one or more controllers in such a tool combination.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 38, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699-Provisional Specification for CIM Framework Domain Architecture) and APC (SEMI E93-0999-Provisional Specification for CIM Framework Advanced Process Control Component) specifications are publicly available from SEMI.

In one embodiment, the present invention is directed to a method of controlling copper polishing processes based upon x-ray fluorescence measurements. In one illustrative embodiment, the method comprises providing a wafer 23 comprised of a layer of insulating material 22 having a barrier metal layer 24 formed thereabove and a layer of copper 26 formed above the barrier metal layer 24, performing a chemical mechanical polishing operation to remove the layer of copper 26 from above the barrier metal layer 24, irradiating at least one area of the wafer 23 with x-rays, and analyzing x-rays leaving the irradiated area to determine the presence of copper. In further embodiments, the method comprises performing additional polishing operations if the analysis of the x-rays leaving the irradiated area indicates the presence of copper. In yet other embodiments, the method comprises stopping the polishing operations based upon the analysis of the x-rays leaving the irradiated area. In still further embodiments, the method comprises determining if the copper polishing operations successfully removed substantially all of the layer of copper based upon the analysis of the x-rays leaving the irradiated area.

In one embodiment, the present invention is directed to a method of controlling barrier metal polishing processes based upon x-ray fluorescence measurements. In one illustrative embodiment, the method comprises providing a wafer 23 comprised of a layer of insulating material 22 having a barrier metal layer 24 formed thereabove, performing a chemical mechanical polishing operation to remove the barrier metal layer material from above the insulating layer 22, irradiating at least one area of the wafer 23 with x-rays, and analyzing x-rays leaving the irradiated area to determine the presence of the barrier metal layer material. In further embodiments, the method comprises performing additional polishing operations if the analysis of the x-rays leaving the irradiated area indicates the presence of the barrier metal layer material. In yet other embodiments, the method comprises stopping the polishing operations based upon the analysis of the x-rays leaving the irradiated area. In still further embodiments, the method comprises determining if the barrier metal polishing operations successfully removed substantially all of the barrier metal layer based upon the analysis of the x-rays leaving the irradiated area.

Through use of the present invention, polishing operations on modern integrated circuit devices may be performed in a more efficient and consistent manner. As a result, overall manufacturing efficiencies may be increased.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   providing a wafer comprised of a layer of insulating material having a layer of barrier metal material formed thereabove;
   performing a chemical mechanical polishing operation to remove said layer of barrier metal material from above said insulating layer;
   irradiating at least one area of said wafer with x-rays; and
   analyzing x-rays leaving said irradiated area to determine the presence of said barrier metal layer material.

2. The method of claim 1, further comprising performing additional polishing operations if the step of analyzing said x-rays indicates that a portion of said barrier metal layer material remains positioned above said insulating layer.

3. The method of claim 1, further comprising stopping said polishing operations on said barrier metal layer material based upon said analysis of said x-rays.

4. The method of claim 1, further comprising determining if said polishing operations successfully removed substantially all of said barrier metal layer material based upon said analysis of said x-rays.

5. The method of claim 1, wherein providing a wafer comprised of a layer of insulating material having a barrier metal layer formed thereabove comprises providing a wafer comprised of a layer of insulating material having a barrier metal layer comprised of at least one of tantalum, tantalum nitride, titanium nitride, tungsten nitride, titanium nitride silicon and tantalum silicon nitride formed thereabove.

6. The method of claim 1, wherein irradiating at least one area of said wafer with x-rays comprises irradiating a plurality of areas of said wafer with x-rays.

7. The method of claim 1, wherein irradiating at least one area of said wafer with x-rays comprises irradiating at least five areas of said wafer with x-rays.

8. The method of claim 1, wherein analyzing x-rays leaving said irradiated area to determine the presence of said barrier metal layer material comprises examining an x-ray spectrum of said x-rays leaving said irradiated area for at least one peak indicating the presence of said barrier metal layer material.

9. A method, comprising:
   providing a wafer comprised of a layer of insulating material having a barrier metal layer comprised of tantalum formed thereabove;
   performing a chemical mechanical polishing operation to remove said layer of tantalum from above said insulating layer;
   irradiating at least one area of said wafer with x-rays; and
   examining an x-ray spectrum of said x-rays leaving said irradiated area)for at least one peak indicating the presence of tantalum.

10. The method of claim 9, further comprising performing additional polishing operations if said examination of said x-ray spectrum indicates that a portion of said layer of tantalum remains positioned above said insulating layer.

11. The method of claim 9, further comprising stopping said polishing operations on said layer of tantalum based upon said examination of said x-ray spectrum.

12. The method of claim 9, further comprising determining if said polishing operations successfully removed substantially all of said layer of tantalum based upon aid examination of said x-ray spectrum.

13. The method of claim 9, wherein irradiating at least one area of said wafer with x-rays comprises irradiating a plurality of areas of said wafer with x-rays.

14. The method of claim 9, wherein irradiating at least one area of said wafer with x-rays comprises irradiating at least five areas of said wafer with x-rays.

15. A method, comprising:
providing a wafer comprised of a layer of insulating material having a barrier metal layer comprised of tantalum formed thereabove;
performing a chemical mechanical polishing operation to remove said layer of tantalum from above said insulating layer;
irradiating a plurality of areas of said wafer with x-rays; and
examining an x-ray spectrum of said x-rays leaving each of said irradiated areas for at least one peak indicating the presence of tantalum.

16. The method of claim 15, further comprising performing additional polishing operations if said examination of said x-ray spectrum for at least some of said irradiated areas indicates that a portion of said layer of tantalum remains positioned above said insulating layer.

17. The method of claim 15, further comprising stopping said polishing operations on said layer of tantalum based upon said examination of said x-ray spectrum for at least some of said irradiated areas.

18. The method of claim 15, further comprising determining if said polishing operations successfully removed substantially all of said layer of tantalum based upon said examination of said x-ray spectrum for at least some of said irradiated areas.

19. The method of claim 15, wherein irradiating a plurality of areas of said wafer with x-rays comprises irradiating at least five areas of said wafer with x-rays.

20. A method of polishing a layer comprised of a barrier layer material in a polishing tool comprised of at least first, second and third polishing platens, comprising:
polishing a wafer comprised of a layer of insulating material having a barrier metal layer comprised of a barrier metal material formed thereabove, and a layer of copper formed above said barrier metal layer;
performing a first polishing operation at said first platen to remove a majority of said layer of copper;
performing a second polishing operation at said second platen remove substantially all of said layer of copper layer remaining above said barrier metal layer after said first polishing operation is performed at said first platen;
performing a third polishing operation at said third platen to remove substantially all of said barrier metal layer material from above said layer of insulating material;
irradiating at least one area of said wafer with x-rays; and
analyzing x-rays leaving said irradiated area to determine the presence of said barrier metal layer material.

21. The method of claim 20, further comprising performing additional polishing operations at said third platen if the step of analyzing said x-rays indicates that a portion of said layer of barrier metal material remains positioned above said insulating layer.

22. The method of claim 20, further comprising stopping said polishing operations on said barrier metal layer at said third platen based upon said analysis of said x-rays.

23. The method of claim 20, further comprising determining if said polishing operations at said third platen successfully removed substantially all of said barrier metal layer based upon said analysis of said x-rays.

24. The method of claim 20, wherein providing a wafer comprised of a layer of insulating material having a barrier metal layer formed thereabove and a layer of copper formed above said barrier metal layer comprises providing a wafer comprised of a layer of insulating material having a barrier metal layer comprised of at least one of tantalum, tantalum nitride, titanium nitride, tungsten nitride, titanium nitride silicon and tantalum silicon formed thereabove and a layer of copper formed above said barrier metal layer.

25. The method of claim 20, wherein irradiating at least one area of said wafer with x-rays comprises irradiating a plurality of areas of said wafer with x-rays.

26. The method of claim 20, wherein irradiating at least one area of said wafer with x-rays comprises irradiating at least five areas of said wafer with x-rays.

27. The method of claim 20, wherein analyzing x-rays leaving said irradiated area to determine the presence of barrier metal layer material comprises examining an x-ray spectrum of said x-rays leaving said irradiated area for at least one peak indicating the presence of said barrier metal layer material.

* * * * *